(12) United States Patent
Singh

(10) Patent No.: US 10,191,021 B2
(45) Date of Patent: Jan. 29, 2019

(54) METHOD FOR ESTIMATING A TEMPERATURE OF A TRANSISTOR

(71) Applicant: Deere & Company, Moline, IL (US)

(72) Inventor: Brij N. Singh, West Fargo, ND (US)

(73) Assignee: DEERE & COMPANY, Moline, IL (US)

( * ) Notice: Subject to any disclaimer, the term of this patent is extended or adjusted under 35 U.S.C. 154(b) by 414 days.

(21) Appl. No.: 14/689,326

(22) Filed: Apr. 17, 2015

(65) Prior Publication Data

US 2016/0252402 A1 Sep. 1, 2016

Related U.S. Application Data

(60) Provisional application No. 62/126,041, filed on Feb. 27, 2015.

(51) Int. Cl.
*G01N 33/00* (2006.01)
*G01R 19/04* (2006.01)
(Continued)

(52) U.S. Cl.
CPC .............. *G01N 33/00* (2013.01); *G01K 7/42* (2013.01); *G01N 2033/0095* (2013.01);
(Continued)

(58) Field of Classification Search
CPC ... G01N 33/00; G01N 2033/0095; G01K 7/42
(Continued)

(56) References Cited

U.S. PATENT DOCUMENTS 3,796,943 A * 3/1974 Nelson ................. G05F 1/5735
323/277
5,497,095 A * 3/1996 Ueyama ............ G01R 27/2605
324/522
(Continued)

FOREIGN PATENT DOCUMENTS

DE 102011003733 A1 8/2012
DE 102012006009 A1 9/2013
(Continued)

OTHER PUBLICATIONS

Chen, Hong Lei. "Protect IGBT's by Sensing Current Using Optical Isolation Amplifiers." Avago Technologies, 2012 [retrieved on Dec. 18, 2013]. Retrieved from the Internet:<http://ww.avagotech.com/docs/AV02-3457EN>.
(Continued)

*Primary Examiner* — Ly D Pham

(57) ABSTRACT

A detector measures turn-off voltage change with respect to change in time between a collector and emitter of a transistor and peak voltage of the transistor at the collector. An electronic data processor determines intermediate parameters of turn-off current, the turn-on current and on-state voltage drop based on the turn-off voltage change and the peak voltage. The data processor determines the power or energy loss for one switching cycle of the transistor based on the turn-off current, the turn-on current and on-state voltage drop between the collector and emitter of the transistor. The data processor estimates an associated average die temperature for the transistor over the switching cycle.

17 Claims, 9 Drawing Sheets

(51) Int. Cl.
  *G01K 7/42* (2006.01)
  *H03K 3/282* (2006.01)
  *H03K 17/68* (2006.01)
(52) U.S. Cl.
  CPC ............ *G01R 19/04* (2013.01); *H03K 3/2821* (2013.01); *H03K 17/68* (2013.01)
(58) Field of Classification Search
  USPC ........................................................ 702/189
  See application file for complete search history.

(56) References Cited

U.S. PATENT DOCUMENTS

| | | | | |
|---|---|---|---|---|
| 6,483,271 | B1* | 11/2002 | Thebeau | H02P 29/02 318/471 |
| 6,816,351 | B1* | 11/2004 | Frank | G01K 3/005 361/103 |
| 7,839,201 | B2* | 11/2010 | Jacobson | G01K 7/42 327/512 |
| 8,760,889 | B2* | 6/2014 | Maruyama | H03K 17/0828 361/93.8 |
| 2005/0088863 | A1 | 4/2005 | Pearce | |
| 2006/0221527 | A1* | 10/2006 | Jacobson | G01K 7/42 361/100 |
| 2009/0279584 | A1* | 11/2009 | Tai | G01K 3/005 374/178 |
| 2010/0150202 | A1 | 6/2010 | Asano et al. | |
| 2013/0009483 | A1* | 1/2013 | Kawate | H02J 3/383 307/77 |
| 2013/0257177 | A1* | 10/2013 | Jacobson | H02M 1/08 307/115 |
| 2015/0168462 | A1 | 6/2015 | Singh | |
| 2016/0036430 | A1* | 2/2016 | Rannestad | H03K 17/0822 363/132 |
| 2016/0118974 | A1* | 4/2016 | Terasawa | H03K 17/18 361/93.8 |

FOREIGN PATENT DOCUMENTS

| | | |
|---|---|---|
| EP | 2444817 A2 | 4/2012 |
| WO | 9810301 A1 | 3/1998 |

OTHER PUBLICATIONS

"Current Sensing Power MOSFETS." Application note [online], NXP Semiconductors, Jun. 24, 2009, Rev. 2 [retrieved on Dec. 18, 2013]. Retrieved from the Internet <URL: http://www.nx.com/documents/application note/AN10322.pdf>.

Domes, Daniel. "IGBT-Module integrated Current and Temperature Sense Features based on Sigma-Delta Converter." Infineon Technologies AG [online] [retrieved on Dec. 18, 2013]. Retrieved from the Internet: <URL: http://www.infineon.com/dgdl/Infineon -Editorial -PCIM Europe 2009 -IGBT Module integrated current and temperature sense features.pdf?folderId= db3a304412b407950112b4095af601 e2&fileId=db3a30432ddc4fc8012d dc7b4bfb0009>.

Donlon, John F. and and Motto, Eric R. "New Compact IGBT Modules with Integrated Current and Temperature Sensors." Powerex Incorporated [online] [retrieved on Dec. 18, 2013]. Retrieved from the Internet: <URL: http://www.pwrx.com/pwrx/app/pet%202005% 2012_ 4.pdf>.

"Fault Detection and Protection." Semikron, Chapter 3, Section 6. pp. 208-210 [online] [retrieved on Dec. 18, 2013]. Retrieved from the Internet: <URL: http://www.semikron.com/skcomub/en/eng_3_ 6_3_1.pdf>.

Lepowski, Jim. "Motor Control Sensor Feedback Circuits." [Application notes] [online]. Microchip Technology Inc., 2003 [retrieved on Dec. 18, 2013]. Retrieved from the Internet: <URL: http://ww1. microchip.com/downloads/en/AppNotes/00894a.pdf>.

Olson, Erik R. and Lorenz, Robert D. "Integrating Giant Magnetoresistive Current and Thermal Sensors in Power Electronic Modules." 18th Annual Applied Power Electronics Conference and Exposition, 2003, vol. 2, pp. 773-777. Institute of Electrical and Electronics Engineers [retrieved on Jan. 3, 2014]. Retrieved from the Internet: <URL: http://ieeexplore.ieee.org/stamp/stamp.jsp?tp=&arnumber= 1179303>. DOI: <10.1109/APEC.2003.1179303>.

Robb, Stephen P.; Taomoto, Aileen A.; and Tu, Larry T. "Current Sensing in IGBTs for Short-Circuit Protection." Proceedings of the 6th International Symposium on Power Semiconductor Devices & ICs, Davos, Switzerland, pp. 81-85 [retrieved on Jan. 3, 2014]. Retrieved from the Internet: <URL: http://ieeexplore.ieee.org/stamp/ stamp.jsp?arnumber=583656>.

Schwarzer, Ulrich; Arens, Andre; and Schulz, Martin. "IGBT Module with integrated Current Measurement Unit Using Sigma-Delta Conversion for Direct Digital Motor Control." Infineon Technologies AG [retrieved on Dec. 18, 2013]. Retrieved from the Internet: <URL: http://www.infineon.com/dgdl/Infineon-PCIM_2010_Module_ integrated_measurements-ED-v1.0-en.pdf?fileId= db3a30432ddc4fc8012ddca3c8fa0036>.

Tam, David. "ICs Protect IGBTs and Sense Currents in Motor Drives." Power Electronics Technology [online], Apr. 2005 [retrieved on Dec. 18, 2013]. Retrieved from the Internet: <URL: http:// powerelectronics.com/mag/504PET22.pdf>.

Sundaramoorthy, V. et al. "Online Estimation of IGBT Junction Temperature (Tj) Using Gate-Emitter Voltage (Vge) at Turn-Off." Institute of Electrical and Electronics Engineers European Conference on Power Electronics and Applications, Sep. 2-6, 2013. <DOI: 10.1109/EPE.2013.6634444>.

Search Report issued in counterpart application No. GB1602438.2, dated Aug. 8, 2016 (3 pages).

* cited by examiner

FIG. 7
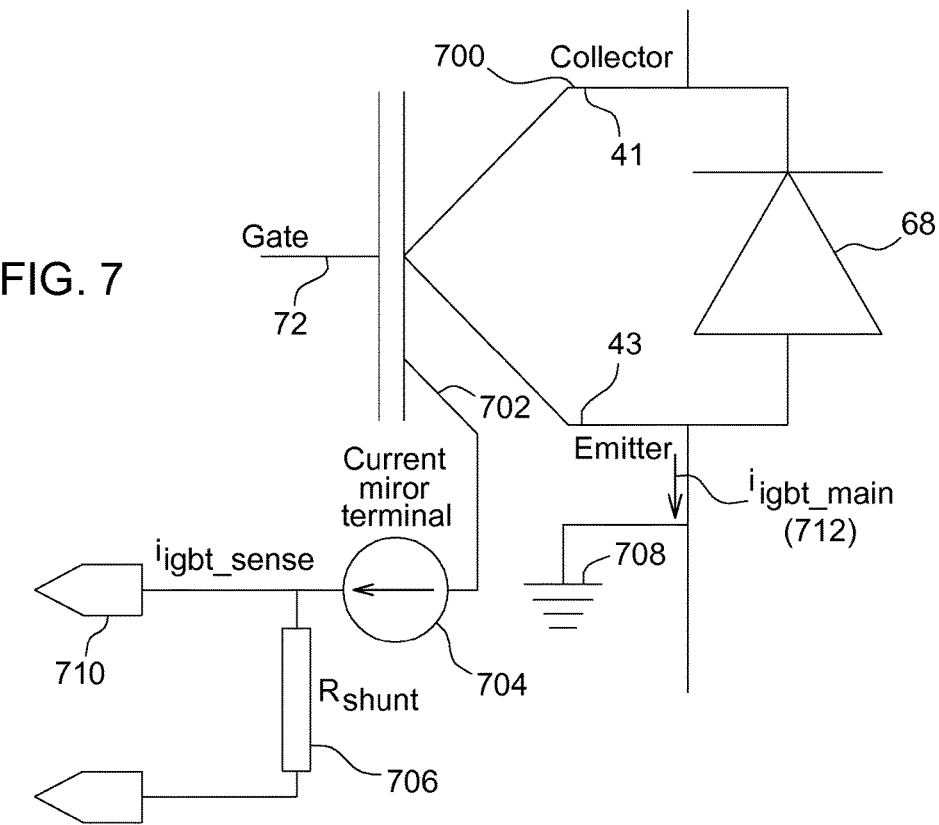
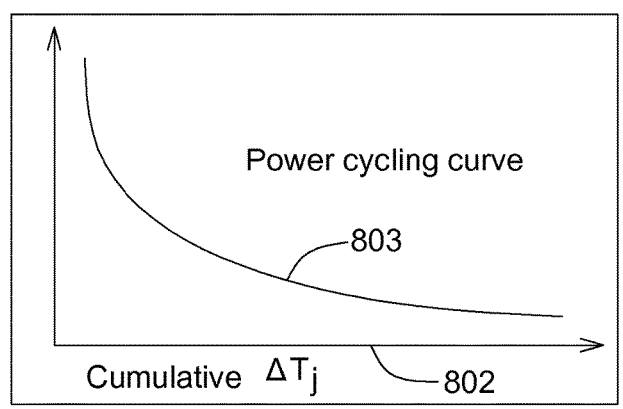
FIG. 8

US 10,191,021 B2

METHOD FOR ESTIMATING A TEMPERATURE OF A TRANSISTOR

This document claims priority based on U.S. provisional application Ser. No. 62/126,041, filed on Feb. 27, 2015 and entitled METHOD FOR ESTIMATING A TEMPERATURE OF A TRANSISTOR, under 35 U.S.C. 119(e).

FIELD

This disclosure relates to a method for estimating a temperature of a transistor; more particularly estimating a junction or die temperature of a transistor.

BACKGROUND

In semiconductor devices, certain prior art temperature sensing schemes use a thermally sensitive resistor spaced apart from the semiconductor die to provide adequate electrical insulation and to reduce noise associated with the semiconductor switching devices. During steady state operation of a transistor using a thermally sensitive resistor (such as a thermistor with a negative temperature coefficient), the estimated junction temperature of the transistor is more accurate than during transient operation, but still not sufficiently accurate for some control applications for inverters that drive electric motors. Thus, there is need for an improved method for estimating junction or die temperature of a transistor in real time that facilitates improved accuracy.

SUMMARY

In accordance with one embodiment, a system and method for estimating junction temperature (of a bipolar junction transistor, channel temperature (of a field effect transistor), or generally die temperature of a semiconductor switching device measures turn-off voltage change (e.g., a rate of voltage rise or $dv_{ce}/dt$) with respect to change in time between a collector and emitter (or drain and source, respectively) of a transistor in a phase of an inverter. A detector measures peak voltage (e.g., $v_{cepeak}$) of the transistor between the collector and the emitter (or drain and source, respectively). An electronic data processor determines intermediate parameters of turn-off current (e.g., $i_{ceturnoff}$), the turn-on current (e.g., $i_{ceturnon}$) and on-state voltage drop (e.g., $v_{ceon}$) based on the turn-off voltage change (e.g., $dv_{ce}/dt$) and the peak voltage (e.g., $v_{cepeak}$). The data processor determines the power or energy loss for one switching cycle of the transistor based on the turn-off current (e.g., $i_{ceturnoff}$), the turn-on current (e.g., $i_{ceturnon}$) and on-state voltage drop (e.g., $v_{ceon}$) between the collector and emitter (or drain and source, respectively) of the transistor. The data processor estimates an associated average junction or die temperature for the transistor over the switching cycle based on the determined energy loss, observed inverter system temperature (e.g., coolant temperature of a coolant in a coolant system) for cooling the inverter, and thermal characteristic of an inverter system (e.g., thermal resistance of a liquid cooled system) for the inverter.

BRIEF DESCRIPTION OF THE DRAWINGS

FIG. 7 is a schematic of a system for sensing a mirror current through a transistor.

FIG. 8 is a chart of a number of power cycles remaining for an inverter versus the change in temperature of its transistors.

DETAILED DESCRIPTION

Figure 1:
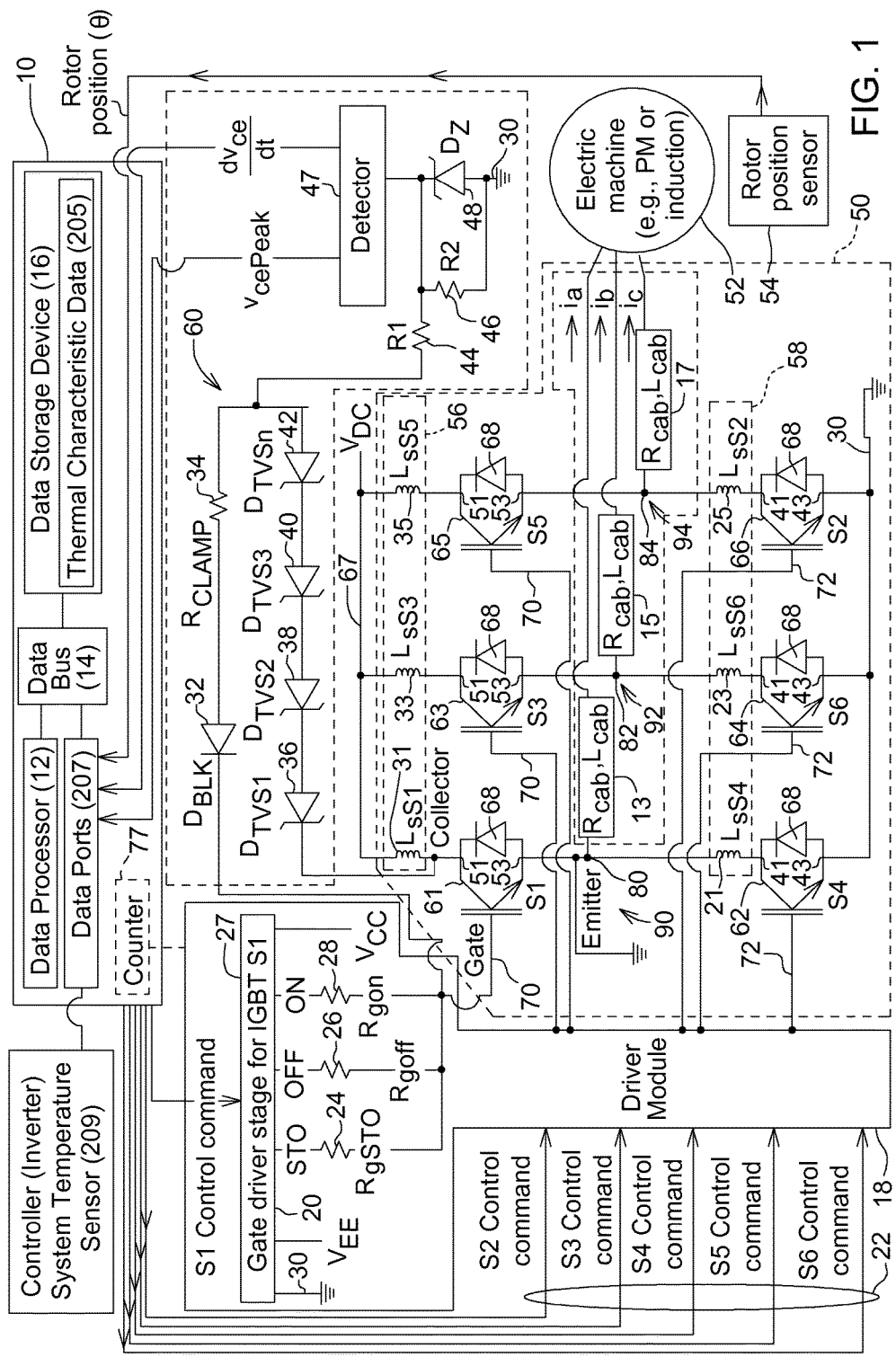
FIG. 1 is a schematic of a system for estimating junction temperature or die temperature of a transistor.

The junction temperature applies to the junction of a bipolar transistor. The die temperature means the junction temperature of a bipolar transistor, or the channel temperature of the depletion or enhancement channel of a field effect transistor, or the die temperature of any other transistor or semiconductor device. The junction temperature or die temperature can be measured over the entire switching cycle or at any instantaneous time during the switching cycle. The die temperature may vary over time during the switching cycle, where the variation is reduced during steady state operation at fixed electrical loads (e.g., inverter load from driving an electric motor at range-bound or constant rotor speed and torque) and static ambient temperature, for example.

The following terminology is used throughout this document:

Transistor Voltages: (1) $v_{ceon}$ means on-state voltage drop or potential (e.g., on state, steady-state voltage drop) between the collector (41, 51) and emitter (43, 53) (or drain and source, respectively), (2) $v_{ce\_turnon}$ means the voltage potential across transistor during turn-on means the voltage drop between the collector (41, 51) and emitter (43, 53) (or drain and source, respectively) during turn on and $v_{ce\_turnon}(t)$ indicates the voltage drop waveform with respect to time; (3) $v_{cepeak}$ means a peak voltage of the transistor between the collector (41, 51) and the emitter (43, 53) (or drain and source, respectively), (4) $dv_{ce}/dt$ means the change in the voltage with respect to time between a collector (41, 51) and emitter (43, 53) (or drain and source, respectively) of a transistor in a phase of an inverter 50; and (5) $v_{ge}$ means the voltage potential between the gate and emitter (43, 53) or between base and the emitter (43, 53).

Transistor Currents: (1) $i_{ceturnoff}$ or $f_{ight\_turnoff}$ means turn-off current; (2) $i_{ceturnon}$ or $i_{ight\_turnon}$ means the turn-on current of a transistor; similarly, and (3) $T_{joff}$ or $T_{j\_turnoff}$ means junction or die temperature during turn-off, and (4) $i_a$ is a first phase current ($i_a$) or, more generally, the current ($i_a$, $i_b$, $i_c$) of one phase (e.g., first phase 90, second phase 92, or third phase 94) of an inverter 50 that flows through the collector-emitter path or source-drain path of the transistor.

FIG. 1 is a schematic of a system for estimating junction temperature or die temperature of a transistor. The temperature estimation system of FIG. 1 can be applied equally to a bipolar junction transistor or a field effect transistor. Further, the system estimation system can be applied to an inverter 50 that uses one or more transistors in conjunction with a liquid-cooled coolant system (e.g., pump and radiator) or an air-cooled system.

In FIG. 1, the system comprises a driver module 18. In one embodiment, the driver module 18 comprises one or more gate driver stages 20 or base drivers to drive corresponding input terminals (e.g., at gate or base 70) of each phase (e.g., first phase 90, second phase 92 and third phase 94) of an inverter 50. An illustrative example of a gate driver stage 20 is shown for first high-side transistor 61 (S1) in FIG. 1. The gate driver stage 20 has a group of resistors (24, 26, 28) connected to an driver output node (e.g., at base or gate 70). In turn, the output node is connected to the gate or base 70 of the first high-side transistor 61 (S1). With respect to the gate driver module 18, other gate driver stages, similar to gate driver stage 20, may be connected in a similar manner to their corresponding transistors (62, 63, 64, 65, 66) within the inverter 50.

Although the inverter 50 of FIG. 1 features three-phases (90, 92, 94), it is understood that the inverter 50 may use or be configured for a single phase or multiple phases in other embodiments that fall within the scope of the appended claims. Each phase of the inverter 50 comprises a pair of transistors, which may be referred to as low-side transistor (62, 64, 66) and a high side transistor (61, 63, 65). The high-side transistor (61, 63, 65) has a collector 51 or drain that is coupled to the high side or positive direct current bus terminal 67 ($V_{DC}$). The low-side transistor (62, 64, 66) has an emitter 43 or source that is coupled to the low side or negative direct current bus terminal (e.g., ground 30). Each phase (90, 92, 94) has a low side input terminal (72) that is the base or gate of the low-side transistor (62, 64, 66) that is fed and controlled by a gate driver module 18. The outputs of the gate module 18 may use one or more resistors to limit the driving current or for impedance matching to the power transistors (61, 62, 63, 64, 65, 66) of the inverter 50. Each phase (90, 92, 94) has a high side input terminal that is the based or gate of the high-side transistor (61, 63, 65) that is fed and controlled by the gate driver module 18. Each phase (90, 92, 94) has an output node (80, 82, 84) that is formed at the junction or coupling of the emitter 53 of one transistor and the collector 41 of the other transistor of the pair of a single phase. In an illustrative embodiment, an optional protective diode 68 may be coupled between the collector (41, 51) and emitter (43, 53) of each transistor, or between the drain and source of any field effect transistor.

In FIG. 1, there is a low-side transistor inductance (21, 23, 35), a high-side transistor inductance (31, 33, 35), an output reactance (13, 15, 17) associated with each phase (90, 92, 94) of the inverter 50. In one embodiment, the output reactance (13, 15, 17) comprises an output cable resistance and an output cable inductance. The low-side transistor inductance (21, 23, 35), the high side transistor inductance (31, 33, 35), the output reactance (13, 15, 17) represent modeled values (or mathematical representations) to model the electric machine 52 (e.g., motor) and the electrical conductor (e.g., cable) that interconnects the inverter 50 and the electric machine 52. Accordingly, in FIG. 1 the modeled values and their respective electrical symbols, for the low-side transistor inductance (21, 23, 35), the high side transistor inductance (31, 33, 35), the output reactance (13, 15, 17), are not physically present as inductors, resistors or other electrical components in working embodiments of the system and such respective electrical symbols may be deleted from certain representations of this embodiment or other embodiments of the system and method for estimating junction temperature or die temperature of a transistor. Here, the electrical symbols and blocks for the modeled values are merely included for explanatory purposes, where their physical realization (to the extent present) are inherent features or characteristics of the transistors and cables between output phase terminals and the electric machine 52.

As illustrated, the electric machine 52 may comprise a motor or a generator with multiple phases. The output node (80, 82, 84) of each phase is connected to the corresponding terminals of the electric machine 52. The electric machine 52 may comprise an electric motor or a generator. For example, the electric machine 52 may comprise a permanent magnet motor or an induction motor. The electric machine 52 may be capable of operating in a motoring mode, a power generation mode, or both. In a motoring mode, the electric machine 52 provides control signals, such as pulse width modulated or other alternating current signals to control the torque, rotor speed, acceleration of a motor. In a power generation mode, the inverter 50 converts generated alternating current to direct current.

The motor or electric machine 52 may be associated with a rotor position sensor 54 or encoder for detecting a position of a rotor of the electric machine 52 or rotor. The rotor position sensor 54 provides rotor position data to a controller 10 for processing.

In one embodiment, the controller 10 may comprise one or more data processors 12, a data bus 14, a data storage device 16, and one or more data ports 207. A data processor 12 may comprise a microcontroller, a microprocessor, a digital signal processor (DSP), an application specific integrated circuit (ASIC), a programmable logic device (PLA), a programmable gate array (PGA), or another electronic data processing device. The data processor 12 is capable of executing software instructions or software stored in or retrieved from the data storage device 16 to estimate junction temperature or die temperature of a transistor in accordance with the method and system described in this disclosure. The data storage device 16 may comprise memory, random access electronic memory, nonvolatile electronic memory, a magnetic storage device, an optical storage device, or another electronic data storage device.

The data storage device 16 may be used to store software, software instructions, measured data, or other data, such as thermal characteristic data 205 for the inverter 50 system (e.g., its liquid or air cooled system), and any equations or look-up tables references in this document.

In one embodiment, an inverter system temperature sensor 209 may provide temperature data or sensor data to the controller 10 via a data port. For example, the temperature sensor 209 may comprise a thermistor or another temperature sensor that provides the coolant temperature of a liquid cooled coolant system for the inverter or the housing temperature of an air-cooled system for the inverter.

At a data port 207, the controller 10 also receives peak voltage measurement data and voltage rise data via a detector 47 that is coupled (directly or indirectly) to at least one of the inverter phases (90, 92, 94). Although one detector 47 is shown as connected to a high-side transistor 61 (S1) at a collector 51 or drain, it is understood that each phase or each transistor may be associated with a corresponding detector (or multiplexed to share a single detector) to facilitate temperature estimation of the respective transistor associated with such phase.

In an alternate embodiment, the controller 10 further comprises an optional counter 77 that is shown in dashed lines to indicate that it is optional and may be deleted in certain configurations. The optional counter 77 can be used to count the number of complete power cycles, pulses, or periods (316) of the respective waveforms 300 (in FIG. 3) of the one or more outputs of the driver module 18 that drive the transistors (61, 62, 63,64, 65, 66).

The detector 47 is associated with ancillary detection circuitry 60. In one embodiment of the detection circuitry 60, a blocking diode 32 ($D_{BLK}$) is coupled to the high-side input (e.g. at gate 70) of the high-side transistor 61 in series with a clamping resistor 34 ($R_{CLAMP}$). A group of avalanche diodes, breakdown diodes, or other multimode diodes (36, 38, 40, 42) are cascaded in series. For example, a multimode diode may comprise Zener diodes or transient voltage suppression (TVS) diodes.

A unidirectional TVS diode is an avalanche diode or multimode diode that: (a) operates in a conventional rectifier mode if forward biased, (b) operates in a direct current blocking mode if reverse biased below the breakdown voltage, and (c) operates in a voltage clamping mode, which can clamp the voltage at a substantially fixed voltage, if reverse biased and above the break-down voltage, where the diode can shunt and withstand very large peak or transient currents without damage in the voltage clamping mode. A Zener diode is a diode can exhibit both Zener breakdown and avalanche breakdown, but does not support the same level of surge suppression of current transients as a TVS diode. A Zener diode or multimode diode operates: (a) in a conventional current blocking mode if forward biased, (b) operates in a direct current blocking mode if reverse biased below the breakdown voltage, and (c) operates in a clamping mode that clamps the voltage at a substantially fixed voltage if reverse biased and above the break-down voltage.

Here, with an insulated gate bipolar transistor (IGBT) (e.g., a PNPN configuration, as illustrated for explanatory purposes without limiting the transistor polarity for general applications of the system), the cathode of the first multimode diode 36 is coupled to the collector 51 or drain. In other embodiments, the transistor (61, 62, 63, 64, 65, 66) may comprise a metal-oxide semiconductor field-effect transistor (MOSFET), a transistor, or other semiconductor, rather than an IGBT. The last multimode diode 42 in the series is coupled to the clamping resistor 34. In turn, the clamping resistor 34 is connected to a voltage dividing resistive network (44, 46) that feeds the detector 47. A Zener diode 48 is parallel with a grounded resistor of the resistive network (44, 46).

In one embodiment, a blocking diode 32 is coupled between the driver module 18 and clamping resistor 34 or the resistive network (44, 46). If a high logic level is applied to the blocking diode 32 from the driver module 18, the blocking diode 32 is reverse biased and blocks a voltage potential from forming across the measurement resistor 46 (R2) or the resistive voltage divider. However, the blocking diode 32 can become forward biased once the resistive network (44, 46) is at or near peak voltage and the driver module 18 output is at a low logic level to discharge the measured voltage across the measurement resistor R2 to low logic signal or ground 30. The TVS diodes (36, 38, 40, 42), clamping resistance (34) and blocking diode (32) collectively function to charge gate-to-source capacitance of transistor 61 when there is excessive voltage across terminals 51 and 53 of transistor 61. As a result of the charging of the gate-to-source capacitance, the voltage across terminals 51 and 53 is snubbed (which means the voltage doesn't go beyond rated voltage value). Accordingly, the circuit of TVS diodes (36, 38, 40, 42), clamping resistance (34) and blocking diode (32) functions as an active clamping circuit.

In one configuration, the detector's (47) measuring of the turn-off change in voltage (or rate or voltage rise)($dv_{ce}$/dt) with respect to change in time is triggered by a drop in the applied voltage from the driver module 18 at gate (e.g., 70) or a drop in $v_{ge}$ to turn-off an active transistor (e.g., 61). Upon a drop in the applied voltage from the driver module 18 at gate (70, 72) or a drop in $v_{ge}$ to turn-off an active transistor (e.g., 61), the detector 47 measures a collector voltage of the transistor (e.g., 61) via a series of cascaded multimode diodes (36, 38, 40, 42) that supply a resistive voltage divider (44, 46), including the measurement resistor 46 (R2). The measurement resistor 46 is in series with Zener diode 48 to limit the voltage magnitude in the measurement resistor 46.

Similarly, in one configuration, the measuring of peak voltage ($v_{cepeak}$) of the transistor is triggered by a drop in the applied voltage from the driver module 18 at gate (70, 72) or a drop in $v_{ge}$, from the driver module 18 to turn-off an active transistor (e.g., 61). Upon a drop in the applied voltage from the driver module 18 at gate (70, 72) or a drop in $v_{ge}$ to turn-off an active transistor (e.g., 61), the detector 47 measures a change (e.g., a pulse or transient spike in) a collector voltage of the transistor (e.g., 61) via a series of cascaded multimode diodes (36, 38, 40, 42) that supply a resistive voltage divider (44, 46), including the measurement resistor 46 (R2).

In an alternate embodiment, the detector may be coupled to the driver module 18 output to trigger the collection of the change in the measured voltage or pulse.

As shown in FIG. 1, the rate of voltage change across resistor 46 (R2) represents rate of rise of transistor turn-off voltage during transistor turn-off (e.g., change in transistor turn-off voltage or $d_{vce}$/dt), or a first transistor parameter. The peak value of voltage across resistor 46 (R2) represents peak value of transient voltage spike or the voltage pulse developed across transistor (e.g., 61) during turn-off event (e.g., $v_{cepeak}$) or a second transistor parameter. In one configuration, the transistor (e.g., 61) is characterized for $d_{vce}$/dt rates over transistor junction temperature from negative 40° C. to positive 175° C. and turn-off time ($t_{off}$) pertaining to each $d_{vce}$/dt rate and transistor junction temperature during turn-off ($T_{off}$); such $d_{vce}$/dt rates and corresponding temperatures are stored in look-up tables, files, inverted files, databases or records in any suitable data structure (e.g., in the data storage device 16 for reference or retrieval by the processor 12).

Figure 2:
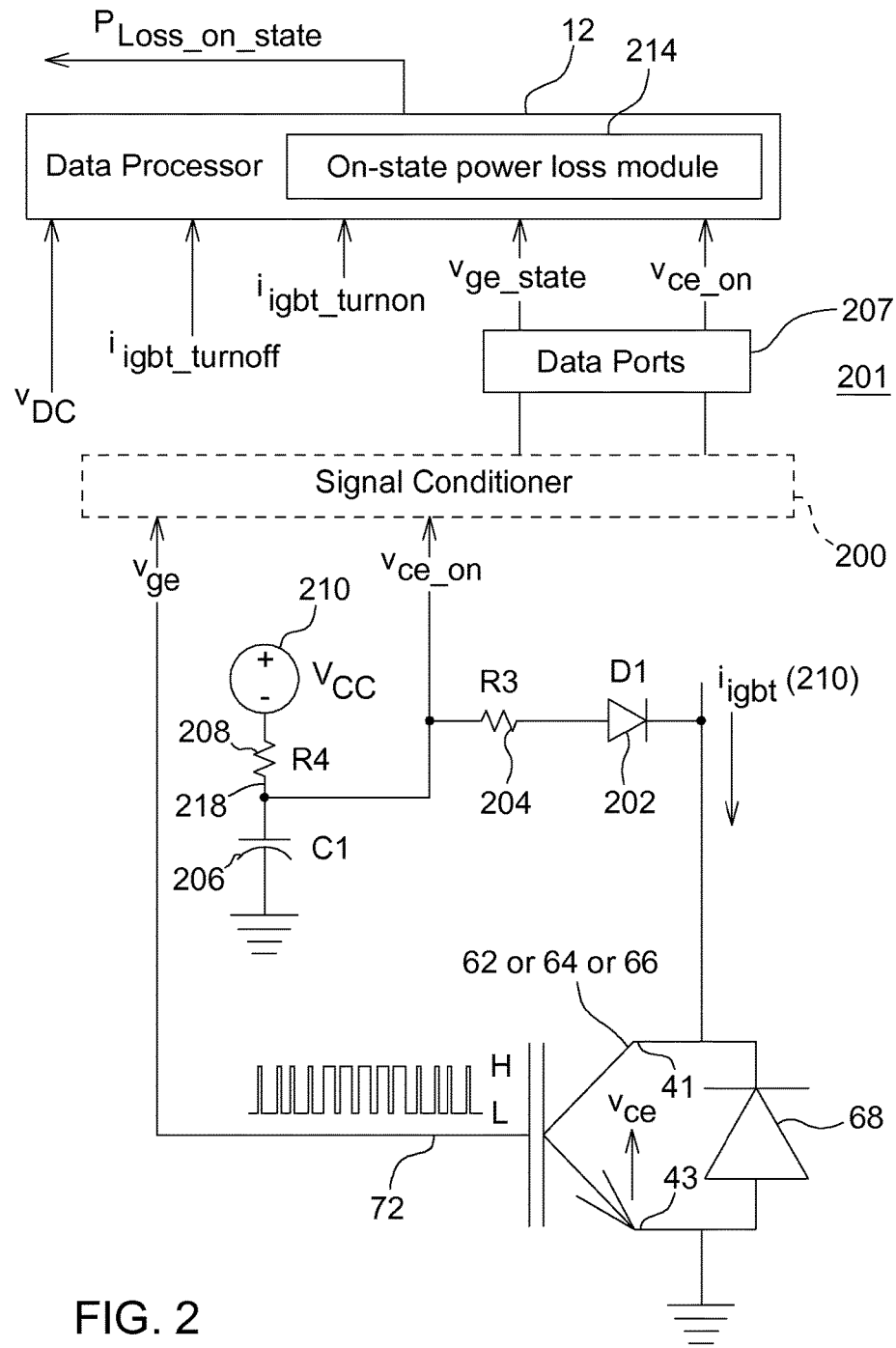
FIG. 2 is a schematic of a system for computing on-state power loss and measuring transistor voltages during an on-state.

FIG. 2 is a schematic of a system 201 for computing on-state power loss and measuring transistor voltages during an on-state. The on-state loss circuit of FIG. 2 can be used in conjunction with any of the transistors (e.g., low-side transistors (62, 64, 66)) of the inverter 50 illustrated in FIG. 1 to determine the voltage drop between the collector 41 and emitter 43 ($v_{ce\_on}$), or between a drain and source, respectively, when the transistor is on consistent with the voltage drop ($v_{ge}$) between the gate 72 or base and the emitter 43. An optional protective diode 68 is connected to the transistor. Like reference numbers in FIG. 1 and FIG. 2 indicate like elements.

A collector 41 terminal of the transistor is associated with diode 202. For example, the collector 41 terminal or drain of the transistor (62, 64, 66) is connected to the cathode of the diode 202 and the anode of the diode 202 is connected in series with a resistor (R3) 204. A voltage source ($V_{CC}$) is connected to a resistor 208 (R4) and capacitor 206 (C1) in series. The node 218 between resistor 208 (R4) and capacitor 206 (C1) is connected to resistor (R3) to provide the $v_{ceon}$ measurement to the data processor 12 via the optional signal conditioner 200 and data ports 207. In FIG. 2, when the transistor (62, 64, 66) is on, the voltage across capacitor 206

(C1) represents on-state voltage drop across transistor denoted as $v_{ce\_on}$. The parameter, $v_{ge}$, is measured at the base or gate 72 terminal of the transistor (62, 64, 66).

In one embodiment, an optional signal conditioner 200 is placed between the on-state loss circuit output and input to the data ports 207 associated with the data processor 12. The optional signal conditioner 200 is indicated as optional because it appears as dashed lines and can be omitted in certain embodiments. The optional signal conditioner 200 may comprise a filter (e.g., low-pass filter), a register, flip-flop, latch, or memory device. The signal conditioner 200 may filter out noise or fluctuations in the measured signals, and/or hold and sample (in a latch, flip-flop or memory device) the voltage parameters (e.g., $v_{ceon}$ and $v_{ge}$) provided by the on-state loss circuit for further processing by the data processor 12.

The data processor 12 of FIG. 1 can receive certain voltage parameters (e.g., $v_{ce\_on}$, $v_{ge}$, $v_{DC}$) at one or more data ports 207 of the controller 10; the data processor 12 can determine or calculate other current parameters (e.g., $i_{igbt\_turnoff}$, $i_{igbt\_turnon}$) as described in this document. The data processor 12 can use the aforementioned voltage parameters (e.g., $v_{ceon}$ and $v_{ge}$) to estimate the on-state power/energy loss for a corresponding transistor (62, 64, 66).

Figure 3:
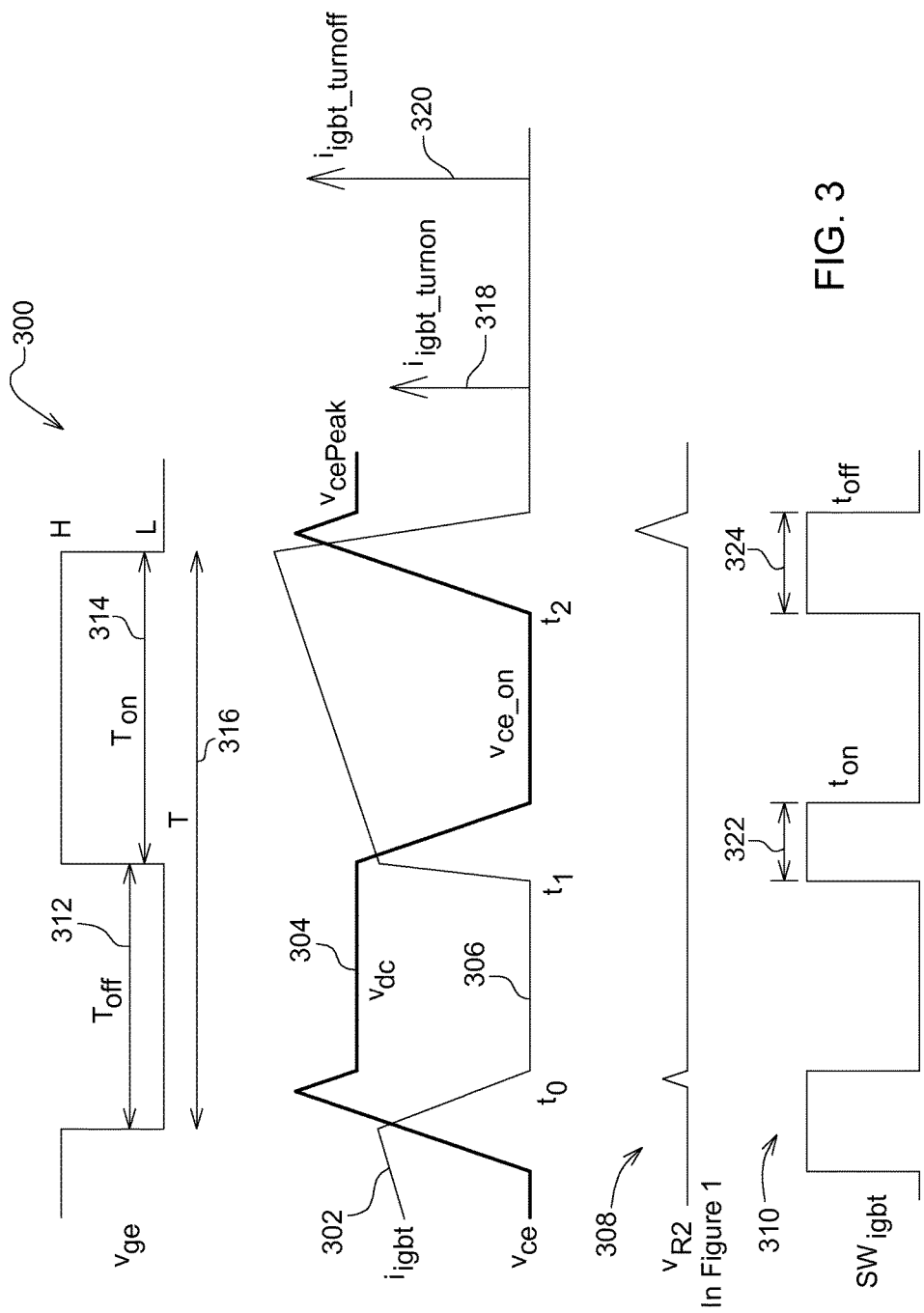
FIG. 3 is a diagram of the waveforms associated with the transistors in an inverter that illustrate a complete switching cycle.

Various waveforms are shown in FIG. 3 for one switching period (T) 316 of a transistor (e.g., low-side or high-side transistor (61, 63, 65)), where the vertical axis represents the amplitude of each waveform and the horizontal axis represents time. As illustrated, the waveforms are synchronized or aligned with respect to each other along the time axis to show the relative relationship of the waveforms in time.

A first waveform 300 represents a transistor base or gate voltage ($v_{ge}$) with on an active interval 314 ($T_{ON}$) and an inactive interval 312 ($T_{OFF}$) over a total cycle or period T. For an NPN or PNPN transistor in an illustrative example, the transistor is off in the inactive interval and on in the active interval.

A second waveform 302 represents a transistor current ($i_{igbt}$) through the emitter (43, 53) and collector (41, 51), or the source and drain, with a first magnitude 318 during turn-on event ($i_{igbt\_turnon}$) and a second magnitude 320 during a turn-off ($i_{igbt\_turnoff}$) event. The second waveform 302 has inflection points at the following times: to, t1, and t2.

A third waveform 304 provides the voltage across the transistor with an off-state voltage as ($v_{DC}$) and on-sate voltage as ($v_{ce\_on}$). A fourth waveform 308 illustrates the voltage across resistance (R2) in FIG. 1 (and may be referred to as $v_{R2}$). A fifth waveform 310 illustrates the turn-on ($t_{on}$) and turn-off ($t_{off}$) time for the transistor. The turn-on ($t_{on}$) and turn-off ($t_{off}$) durations are consistent with the other waveforms of FIG. 3 and merely representative of possible waveforms of transistors in accordance with this disclosure.

Figure 4:
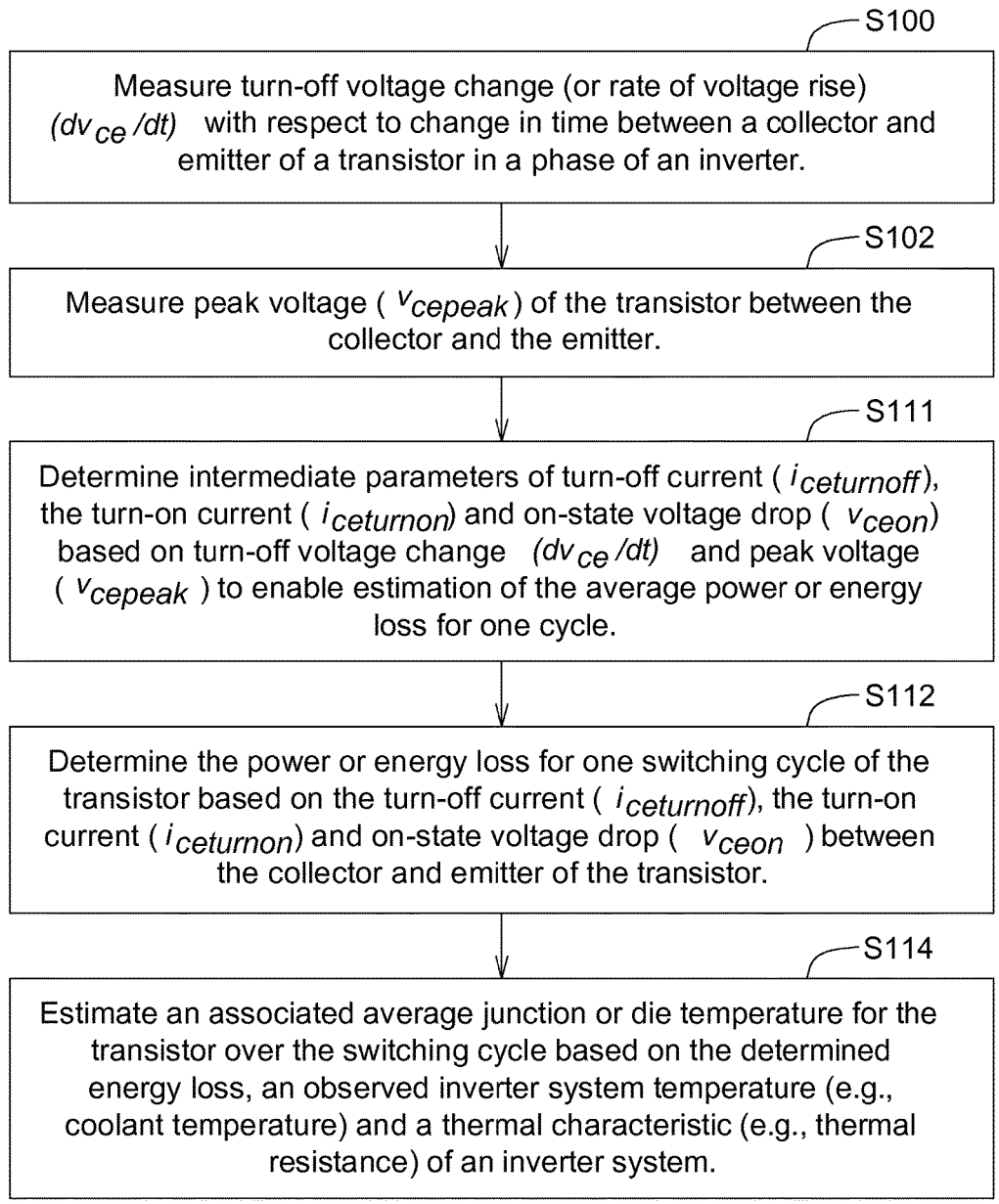
FIG. 4 is flow chart of one embodiment of a method for estimating junction temperature or die temperature of a transistor.

In accordance with one embodiment, FIG. 4 illustrates a flow chart of one embodiment of a method for estimating junction temperature or die temperature of a transistor.

In step S100, a detector 47, alone or in conjunction with the detection circuitry 60, measures turn-off voltage change ($dv_{ce}/dt$) with respect to change in time between a collector (41, 51) and emitter (43, 53) (or between a drain and source) of a transistor (61, 62, 63, 64, 65, 66) in a phase (90, 92, 94) of an inverter 50. The turn-off voltage change may also be referred to as a rate of voltage rise between a collector (41, 51) and emitter (43, 53) (or between a drain and source) of a transistor in a phase of an inverter 50. In one embodiment, in response to the gate driver signal from the driver module 18, a change or drop in $v_{ge}$ to turn off an active transistor triggers the detector 47 to measure the turn-off change in voltage (or rate or voltage rise of a pulse or transient spike) ($dv_{ce}/dt$) with respect to change in time; and the detector 47 to measure a voltage potential ($v_{ce}$) between the collector (41, 51) and emitter (43, 53), or between the drain and source, of the transistor via a series of cascaded multimode diodes (36, 38, 40, 42) and a resistive voltage divider (44, 46). For example, the detector 47 can measure the turn-off change in voltage (or rate or voltage rise of a pulse or transient spike) ($dv_{ce}/dt$) with respect to change in time at or across measurement resistor 46.

In step S102, a detector 47, alone or in conjunction with the detection circuitry 60, measures peak voltage ($v_{cepeak}$) of the transistor between the collector (41, 51) and the emitter (43, 53), or between the source and the drain. For example, in response to the gate driver signal from the driver module 18, a change or drop in $v_{ge}$ to turn off an active transistor (61, 62, 63, 64, 65, 66) triggers the detector 47 to measure peak voltage ($v_{cepeak}$) of a pulse or transient spike of the transistor via a series of cascaded multimode diodes (36, 38, 40, 42) and a resistive voltage divider (44, 46). For example, the detector 47 can measure the turn-off change in voltage peak voltage ($v_{cepeak}$) of a transient spike or pulse at or across measurement resistor 46.

In step S111, an electronic data processor 12 determines intermediate parameters of turn-off current ($i_{ceturnoff}$), the turn-on current ($i_{ceturnon}$) and on-state voltage drop ($v_{ceon}$) based on the turn-off voltage change ($dv_{ce}/dt$) and the peak voltage ($v_{cepeak}$) to enable estimation of the average power or energy loss for one cycle.

In step S112, the data processor 12 determines the power or energy loss for one switching cycle of the transistor based on the turn-off current ($i_{ceturnoff}$), the turn-on current ($i_{ceturnon}$) and on-state voltage drop ($v_{ceon}$) between the collector (41, 51) and emitter (43, 53) or between the drain and source, of the transistor.

In step S114, the data processor 12 estimates an associated average junction or average die temperature for the transistor (61, 62, 63, 64, 65, 66) over the switching cycle (e.g., period 316) based the on the determined energy loss, an observed inverter system temperature (e.g., coolant temperature of a coolant in a coolant system) for cooling the inverter 50, and a thermal characteristic of an inverter system (e.g., thermal resistance of a liquid cooled system) for the inverter 50. An average junction or die temperature may represent a mean junction or die temperature, a median junction or die temperature, or a mode junction or die temperature. The method or temperature estimation can be applied to an inverter 50 that uses one or more transistors in conjunction with a liquid-cooled coolant system (e.g., pump and radiator) or an air-cooled system. For a liquid-cooled system, the temperature sensor 209 provides a coolant temperature, whereas for an air-cooled system, the temperature sensor 209 provides a housing temperature of the inverter 50. The liquid-cooled system may be associated with a first set of thermal characteristic data 205 (e.g., first thermal resistance), whereas the air-cooled system may be associated with a second set of thermal characteristic data 205 (e.g., second thermal resistance), where the first set is distinct from the second set. The thermal characteristic data 205 is stored in the data storage device 16 for retrieval and processing by the data processor 12.

Figure 5:
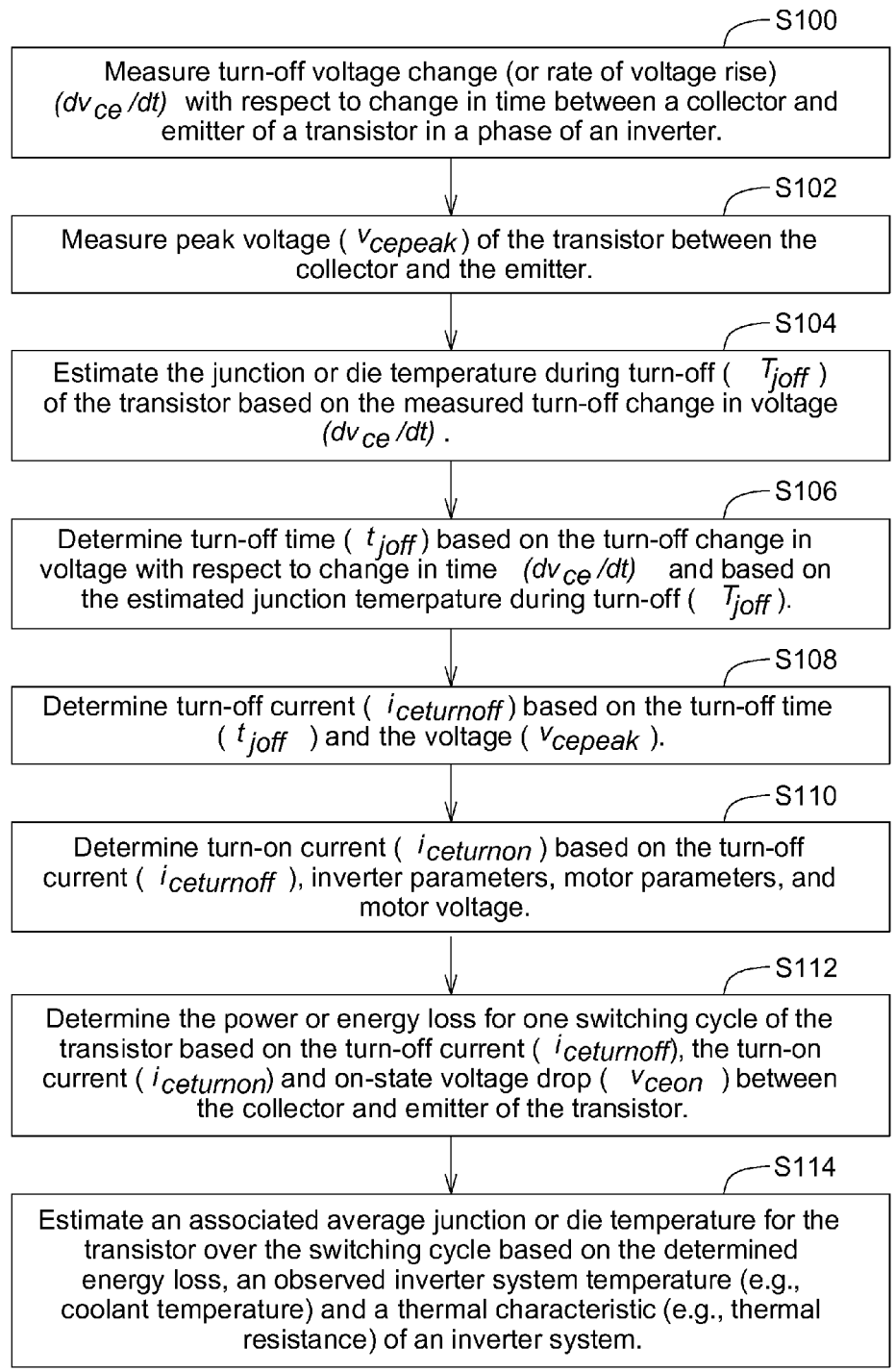
FIG. 5 is flow chart of another embodiment of a method for estimating junction temperature or die temperature of a transistor.

In accordance with one embodiment, FIG. 5 illustrates a flow chart of another embodiment of a method for estimating junction temperature or die temperature of a transistor. The method of FIG. 5 is similar to the method of FIG. 4, except the method of FIG. 5 replaces step S111 of FIG. 4 with steps S104, S106, S108 and S110. Like reference numbers indicate like steps or procedures.

In step S100, a detector 47, alone or in combination with the detection circuitry 60, measures turn-off voltage change (or rate of voltage rise) ($dv_{ce}/dt$) with respect to change in time between a collector (41, 51) and emitter (43, 53), or between a drain and source, respectively, of a transistor (61, 62, 63, 64, 65, 66) in a phase (90, 92, 94) of an inverter 50.

In step S102, a detector 47, alone or in connection with the detection circuitry 60, measures peak voltage ($v_{cepeak}$) of the transistor between the collector (41, 51) and the emitter (43, 53).

In step S104, the data processor 12 estimates the junction or die temperature during turn-off ($T_{joff}$ or $T_{j\_turnoff}$) of the transistor (61, 62, 63, 64, 65, 66) of step S100 based on the measured turn-off change in voltage ($dv_{ce}/dt$). The transistor junction temperature is computed as stated in Equation 1:

$$T_{j\_turnoff} = fn\left(\frac{dv_{ce}}{dt}\right) \quad (1)$$

In one configuration, the transistor is characterized for $d_{vce}/dt$ rates over transistor junction temperature or die temperature over an operational range (e.g., from approximately negative 40° C. to approximately positive 175° C.). For example, prior to executing step S104 or prior to executing the method of FIG. 5, the transistor is characterized for one or more of the following: (1) a respective turn-off time ($t_{off}$) pertaining to each $d_{vce}/dt$ rate, or (2) a corresponding transistor junction temperature, or die temperature, during turn-off ($T_{joff}$) pertaining to each $d_{vce}/dt$ rate. The $d_{vce}/dt$ rates, a respective turn-off time ($t_{off}$), and die temperature ($T_{joff}$) maybe stored in look-up tables, files, inverted files, databases or records in any suitable data structure in the data storage device 16 for retrieval to execute Equation 1.

In step S106, the data processor 12 determines turn-off time ($t_{off}$) of the transistor based on the turn-off change in voltage with respect to change in time ($dv_{ce}/dt$) and based on the estimated junction temperature during turn-off ($T_{off}$). Junction temperature dependent turn-off time of transistor is stated as in Equation 2:

$$t_{off} = fn\left(\frac{dv_{ce}}{dt} \text{ and } T_{j\_turnoff}\right) \quad (2)$$

Step S106 may be executed in accordance with various techniques, which may be applied separately and cumulatively. Under a first technique, the above function in Equation 2 is a polynomial equation that is based on off-line characterization of transistor. For example, off-line characterization means obtaining or collecting characteristics data or the characterization (e.g., at factory, laboratory, or electronics testing facility or from the transistor manufacturer) prior to commercial distribution of the transistor in the inverter 50 or prior to operation of the transistor by an end user. The characterization data or characterization may be stored in the data storage device 16 for retrieval and processing by the data processor 12.

Under a second technique, the above function in Equation 2 is determined as follows. For example, prior to executing step S106 or prior to executing the method of FIG. 5, the transistor is characterized for one or more of the following: (1) a respective turn-off time ($t_{off}$) pertaining to each $d_{vce}/dt$ rate, or (2) a corresponding transistor junction temperature during turn-off ($T_{off}$) pertaining to each $d_{vce}/dt$ rate. The $d_{vce}/dt$ rates, a respective turn-off time ($t_{off}$), and die temperature ($T_{joff}$) maybe stored in look-up tables, files, inverted files, databases or records in any suitable data structure in the data storage device 16 for retrieval and processing by the data processor 12 to execute Equation 2.

In step S108, the data processor 12 determines turn-off current ($i_{ceturnoff}$) based on the turn-off time ($t_{off}$) and the peak voltage ($v_{cepeak}$). Once turn-off time ($t_{off}$) is determined using dv/dt rate and junction temperature during turn-off event, transistor current during turn-off event is determined as per Equation 3:

$$i_{igbt\_turnoff} = \int_0^{t_{off}} \left(\frac{v_{cepeak} - v_{DC}}{L_{sIGBT}}\right)dt \quad (3)$$

In Equation 3, $v_{cepeak}$ is peak voltage across transistor during turn-off, $v_{DC}$ is the direct current (DC) bus voltage of inverter 50, and $L_{sIGBT}$ is inductance associated with the transistor (e.g., stray inductance involving the circuit path that has inverter direct current (DC) bus and internal bus-bar within transistor to the collector (41, 51) terminal or drain terminal).

In step S110, the data processor 12 determines turn-on current ($i_{ceturnon}$) based on the turn-off current ($i_{ceturnoff}$), inverter 50 parameters, motor parameters, and motor voltage. To calculate transistor current during a turn-on event, Equations 11 and 12 can be used. The Equations 11 and 12 assume phase A high-side transistor (61, 63, 65), e.g., transistor S1, in FIG. 1 is turning off approximately at time $t_2$ and is turning on at approximately time $t_1$, consistent with waveforms 300 and 302 in FIG. 3. In the execution of step S110, Equation (10) can be solved for $i_a$ as follows:

$$v_{DC} = R_S i_a + L_S \frac{d}{dt}i_a + \omega_e \Psi_m \sin(\theta_e) = \quad (10)$$

$$R_S i_a + L_S \frac{d}{dt}i_a + \omega_e \Psi_m \sin(\omega_e t)$$

$$i_a = \int_{t_1}^{t_2}\left(\frac{v_{DC} - R_S i_a - \omega_e \Psi_m \sin(\omega_e t)}{L_S}\right)dt \quad (11)$$

$$i_a(t)_{at\,t_2} = i_{igbt\_turnoff} \quad (12)$$

For background purposes, Equations 10 through 12, which can be used in step S110, are derived based on the following Equations 4 through 9, which after their derivation do not need to be used again:

$$v_{DC} = Ri_a + L\frac{d}{dt}i_a + E_a \quad (4)$$

In Equation (4) $i_a$ is phase-A current through transistor (S1 or S4), $E_a$ is phase-A back EMF (electromotive force) and R and L are made of cable and machine winding electrical parameters as stated below:

$$R = R_{cab} + R_S \quad (5)$$

$$L = L_{cab} + L_S \quad (6)$$

where $R_{cab}$ is the cable resistance between the phase output terminal and the electric machine 52, and $L_{cab}$ is the cable inductance between the phase output terminal and the electric machine 52, $R_s$ is the resistance of the of the transistor at the collector (41, 51) terminal and $L_s$ is the inductance of the transistor at the collector (41, 51) terminal.

Because cable electrical parameters are far smaller than electric machine parameters, therefore, $$R \approx R_S \text{ and } L \approx L_S \quad (7)$$

Electric machine 52 is assumed to be PMSM (permanent magnet sinusoidal machine). Back EMF for phases a, b and c ($E_a$, $E_b$ and $E_c$, respectively) is defined in Equation 8.

$$\begin{bmatrix} E_a \\ E_b \\ E_c \end{bmatrix} = \omega_e \Psi_m \begin{bmatrix} \sin(\theta_e) \\ \sin\left(\theta_e - \frac{2\pi}{3}\right) \\ \sin\left(\theta_e + \frac{2\pi}{3}\right) \end{bmatrix} \quad (8)$$

In Equation 8, $\omega_e$ is electrical speed of rotor in rad/second, $\Psi_m$ is amplitude of magnetic flux and this parameter is known to motor control system for over a range of rotor temperature and $\theta_e$ is electrical position of electric machine rotor of the electric machine 52. $\theta_e$ is rotor position is made available using sensor as shown in FIG. 1. Also, $\omega_e$ is expressed as per Equation 9.

$$\omega_e = \frac{d}{dt} \theta_e \quad (9)$$

Using Equations 5-9, Equation 4 is modified as stated in Equation 10.

In the execution of step S110, Equation 10 can be solved for $i_a$:

$$v_{DC} = R_S i_a + L_S \frac{d}{dt} i_a + \omega_e \Psi_m \sin(\theta_e) = \quad (10)$$

$$R_S i_a + L_S \frac{d}{dt} i_a + \omega_e \Psi_m \sin(\omega_e t)$$

$$i_a = \int_{t_1}^{t_2} \left( \frac{v_{DC} - R_S i_a - \omega_e \Psi_m \sin(\omega_e t)}{L_S} \right) dt \quad (11)$$

$$i_a(t)_{at\,t_2} = i_{igbt\_turnoff} \quad (12)$$

$$i_a(t)_{at\,t_1} = i_{igbt\_turnon}$$

Using Equations 11 and 12, $i_a(t)$ can be obtained at instant $t_1$ and that would be transistor current during turn-on event ($i_{igbt\_turnon}$) in a switching cycle of transistor.

In step S112, the data processor 12 determines the power or energy loss for one switching cycle of the transistor based on the turn-off current ($i_{ceturnoff}$), the turn-on current ($i_{ceturnon}$) and on-state voltage drop ($v_{ceon}$) between the collector (41, 51) and emitter (43, 53) of the transistor, or between the drain and source of the transistor. Once transistor turn-on current is determined, transistor turn-on time is calculated using polynomial and this polynomial is based turn-on junction temperature dependent pre-characterize data of transistor.

$$t_{on} = fn(i_{igbt\_turnon} \text{ and } T_{j(n-1)}) \quad (13)$$

It is noted that voltage across transistor will fall with a rate decided by turn-on time of transistor, e.g., $t_{on}$. Therefore, rate of fall of voltage across transistor during turn-on is defined as below:

$$v_{ce\_turnon}(t) = \frac{v_{DC}}{t_{on}}(t) \quad (14)$$

Determination of Power Losses in the Transistor transistor energy losses during turn-on, turn-off and on-state events are stated as per Equations 15, 16 and 17, respectively.

Turn-on switching energy loss ($E_{on}$): $E_{on}$ is stated as per equation (15)

$$E_{on} = v_{DC} \times i_{igbt\_turnon} \times t_{on} \quad (15)$$

Turn-on switching energy loss ($E_{off}$): $E_{off}$ is stated as per Equation 16:

$$E_{off} = v_{DC} \times i_{igbt\_turnoff} \times t_{off} \quad (16)$$

Over one switching period transistor current varies as per simplified waveform depicted in FIG. 3.

On state energy loss ($E_{on\_state}$): $E_{on\_state}$ is stated as per equation 17 as follows:

$$E_{on\_state} = v_{ce\_on} \times (0.5 \times i_{igbt\_turnon} + 0.5 \times i_{igbt\_turnoff}) \times T_{ON} \quad (17)$$

It is noted that average of turn-on ($i_{igbt\_turnon}$) and turn-off ($i_{igbt\_turnoff}$) currents are considered to determine on-state energy loss in the transistor.

Total energy loss during one switching period of the transistor is sum of turn-on switching energy, turn-off switching energy, and on-state energy loss.

$$E_{Loss} = k_1(v_{DC} \times i_{igbt\_turnon} \times t_{on}) + k_2(v_{DC} \times i_{igbt\_turnoff} \times t_{off}) + 0.5 k_3(v_{ce\_on} \times (i_{igbt\_turnon} + i_{igbt\_turnoff}) \times T_{ON} \quad (18)$$

In Equation (18), constants $k_1$, $k_2$ and $k_3$ are determined by characterizing the applicable transistor in an inverter 50 or in an inverter-driven electric machine system.

Average power lost in the transistor during one switching interval is stated as below:

$$P_{Loss} = E_{Loss}/T$$

Before switching loss is calculated it is important to describe switching waveforms over a switching period of transistor.

In step S114, the data processor 12 estimates an associated average junction or average die temperature for the transistor over the switching cycle based the on the determined energy loss, an observed inverter system temperature (e.g., coolant temperature of a coolant in a coolant system) for cooling the inverter 50, and a thermal characteristic of an inverter system (e.g., thermal resistance of a liquid cooled system) for the inverter 50. An average junction or die temperature may represent a mean junction or die temperature, a median junction or die temperature, or a mode junction or die temperature. The method or temperature estimation can be applied to an inverter 50 that uses one or more transistors in conjunction with a liquid-cooled coolant system (e.g., pump and radiator) or an air-cooled system. For a liquid-cooled system, the temperature sensor 209 provides a coolant temperature, whereas for an air-cooled system, the temperature sensor 209 provides a housing temperature of the inverter 50. The liquid-cooled system may be associated with a first set of thermal characteristic data 205 (e.g., first thermal resistance), whereas the air-cooled system may be associated with a second set of thermal characteristic data 205 (e.g., second thermal resistance), where the first set is distinct from the second set.

In one embodiment, Thermal resistance ($R_{jc}$) of transistor thermal management is assumed X° C./Watt. For liquid cooled power electronics systems X could vary in the range 0.1 to 0.3. Average junction temperature of transistor over one switching period is stated as below;

$$T_j = T_{coolant} + P_{Loss} R_{jc}$$

Coolant temperature is provided by the temperature sensor 209, or by an inverter control system, or by a vehicle control unit where the inverter 50 is deployed to control vehicle drive or traction systems. If the vehicle control unit or engine controller 10 provides the coolant temperature it may be communicated to the controller 10 via a vehicle data bus 14 (e.g., controller area network (CAN) data bus, Ethernet, or another data bus).

Figure 6A:
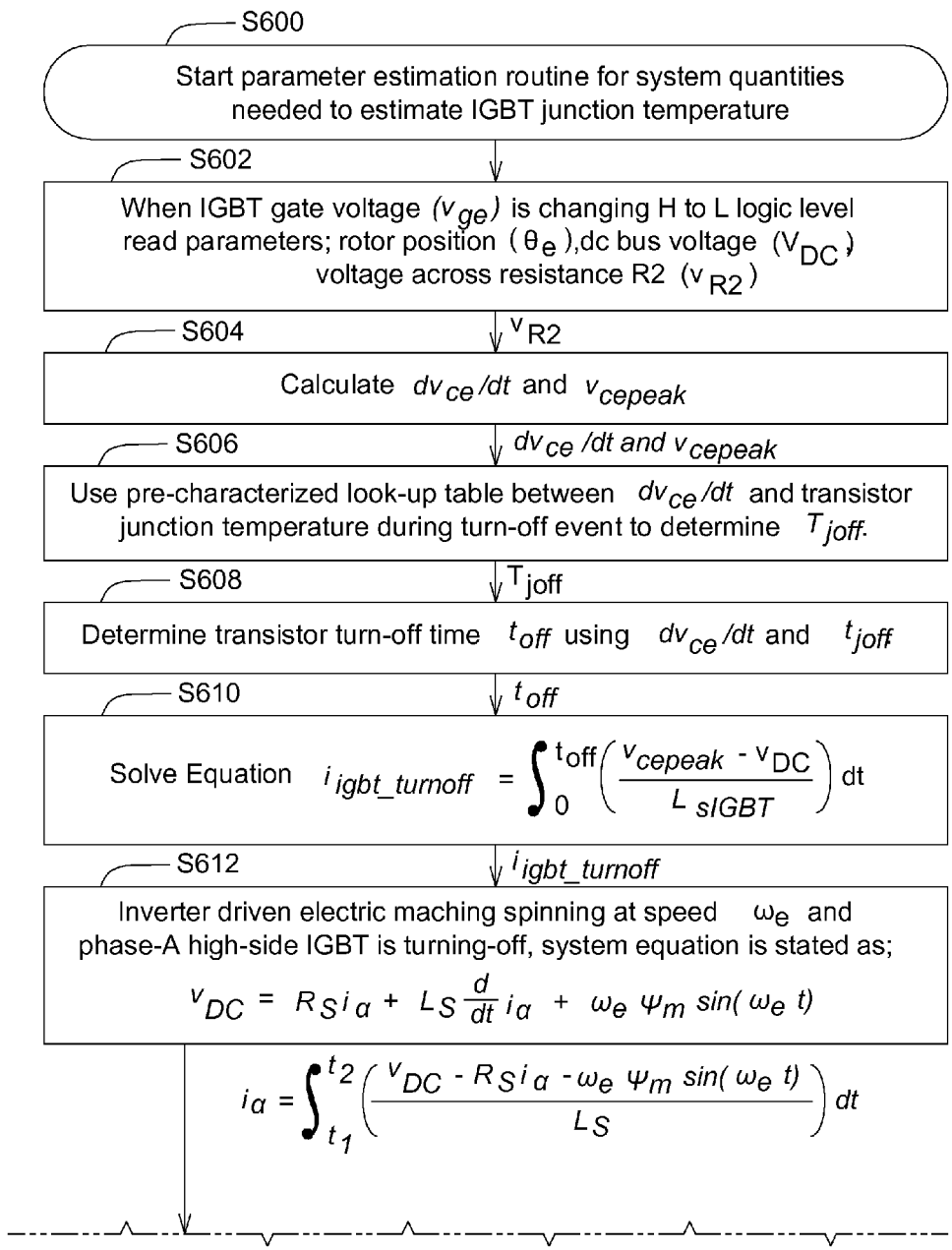
FIG. 6, which collectively refers to FIG. 6A and FIG. 6B, is flow chart of yet another embodiment of a method for estimating junction temperature or die temperature of a transistor.
Figure 6B:
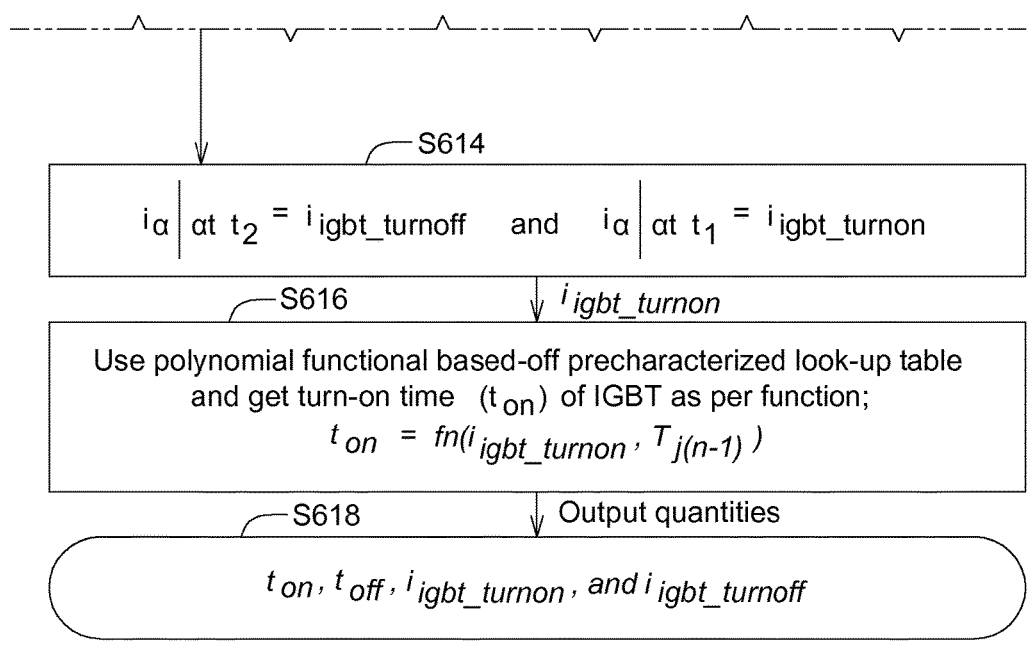

FIG. 6 is flow chart of yet another embodiment of a method for estimating junction temperature or die temperature of a transistor. The method is similar to the method of FIG. 5 except some additional details are presented. The flow chart of FIG. 6 represents an algorithm that is used to determine parameters and quantities needed for transistor energy loss estimation.

In step S600, the data processor 12 starts the parameter estimation routine for system quantities needed to estimate transistor junction temperature.

In step S602, when the transistor gate voltage ($v_{ge}$) is changing high (H) logic level to low (L) logic level, read the following parameters: rotor position ($\theta_e$) from the rotor position sensor 54, direct current ($V_{DC}$) bus voltage from a voltage measuring circuit (e.g., comparator), and voltage ($V_{R2}$) across resistor (R2) in FIG. 1.

In step S604, the detector 47 measures or determines $dv_{ce}/dt$ and $v_{cepeak}$. For example, the detector 47, alone or in conjunction with the detection circuitry, measures or determines $dv_{ce}/dt$ in accordance with step S100 and $v_{cepeak}$ in accordance with step S102.

In step S606, the data processor 12 uses a first look-up table, first file, or first data structure to determine transistor junction temperature ($T_{joff}$) based on the determined $d_{vce}/dt$, where the lookup table defines the relationship between dvce/dt and junction temperature during a turn-off event ($T_{joff}$). The first look-up table, first file, or first data structure can be stored in the data storage device 16 and can be pre-determined or determined based on the characteristics of the transistor prior to execution of the method of FIG. 6.

In step S608, the data processor 12 determines transistor turn-off time ($t_{off}$) based on $dv_{ce}/dt$ and the transistor junction temperature $T_{joff}$.

In step S610, the data processor 12 solves an equation (e.g., Equation 3) for $i_{ight\_turnoff}$. For example, the equation for $i_{ight\_turnoff}$ is based on the following integral, where the integral is taken of the time period from t equals 0 to t equals $t_{off}$ from step S608.

$$i_{igbt\_turnoff} = \int_0^{t_{off}} \left( \frac{v_{cepeak} - v_{DC}}{L_{sIGBT}} \right) dt$$

In step S612, the data processor 12 considers the load or electric machine 52 that is driven by the inverter 50, which comprises two transistors per phase of the inverter 50. For example, the electric machine 52 may be characterized as the following equation (e.g., Equation 10):

$$v_{DC} = R_S i_a + L_S \frac{d}{dt} i_a + \omega_e \Psi_m \sin(\theta_e) = R_S i_a + L_S \frac{d}{dt} i_a + \omega_e \Psi_m \sin(\omega_e t)$$

In step S614, the data processor 12 determines the current of a phase at a transistor turn-off time ($t_2$) and the current of the phase a transistor turn-on time ($t_1$) in accordance with the following equations (e.g., Equations 11 and 12).

$$i_a = \int_{t_1}^{t_2} \left( \frac{v_{DC} - R_S i_a - \omega_e \Psi_m \sin(\omega_e t)}{L_S} \right) dt \quad (11)$$

$$i_a(t)_{at\, t_2} = i_{igbt\_turnoff} \quad (12)$$
$$i_a(t)_{at\, t_1} = i_{igbt\_turnon}$$

In step S616, the data processor 12 uses a polynomial function based on a second look-up look-up table, second file, or second data structure to get a turn-on time ($t_{on}$) of the transistor as a function: $t_{on}$=fn ($i_{igbt\_turnon}$, $T_{j(n-1)}$). The second look-up table, second file, or second data structure can be stored in the data storage device 16 and can be pre-determined or determined based on the characteristics of the transistor prior to execution of the method of FIG. 6.

In step S618, the data processor 12 outputs the parameters or quantities $t_{on}$, $t_{off}$, $i_{igbt\_turnon}$ and $i_{igbt\_turnoff}$ for determination of the transistor energy loss during a cycle. The quantities from step S618 may be used in steps S112 and S114 to estimate an associated average junction or die temperature over a switching cycle of the transistor.

FIG. 7 is a schematic of a system for sensing a mirror current ($i_{igbt\_sense}$) through a transistor 700, where transistor 700 can be substituted for any transistor (61, 62, 63, 64, 65, 66) in FIG. 1, for example. The current mirror circuit (e.g., 702, 704, 706) of FIG. 7 facilitates cross checking the value of $i_{igbt\_turnoff}$ and $i_{igbt\_turnon}$ currents determined in accordance with the methods of FIG. 4, FIG. 5 or FIG. 6. The current mirror circuit of FIG. 7 requires a transistor 700 that is manufactured with current mirror associated with the collector-to-emitter path or drain-to-source path. The current mirror produces a mirror current or secondary current ($i_{igbt\_sense}$) that is a small fraction (e.g., less than one percent) of the main current ($i_{igbt\_main}$) flowing through transistor 700 between the collector 41 and emitter 43. A current mirror may be modeled as a current source 704 where the value of current supplied by this current source 704 is proportional to the main current ($i_{igbt\_main}$) flowing through the transistor 700. The mirror current associated with the current source 704 is accessible via an additional terminal 702 on the transistor 700.

The mirror current flows through a properly sized (ohm value and watt ratings) resistor 706 ($R_{shunt}$). The voltage across the resistor $R_{shunt}$ is measured (e.g., at terminal 710) and is proportional to the mirror current (e.g., $i_{igbt\_sense}$). The mirror current $i_{igbt\_sense}$ during IGBT turn-off is proportional to the main turn-off current, $i_{igbt\_turnoff}$, and during IGBT turn-on the mirror current is proportional to the main turn-on current, $i_{igbt\_turnon}$. The data processor 12 can receive the observed mirror current (or the corresponding voltage across resistor 706) via one or more data ports 207, or a signal conditioner coupled to a data port 207. In one embodiment, the data processor 12 uses the observed mirror current of a transistor 700 to cross-check the correctness and accuracy of estimated $i_{igbt\_turnoff}$ and $i_{igbt\_turnon}$ in accordance with any method, step or process disclosed in this document. For example, the data processor 12 can determine the cross-correlation (or deviation of any proportionality constant) between the corresponding mirror current values and estimated $i_{igbt\_turnoff}$ and $i_{igbt\_turnon}$ in accordance with any method, step or process disclosed in this document.

In one embodiment, the data processor 12 measures the turn-on and turn-off mirror currents to cross-check the correctness and accuracy of the determined turn-on current ($i_{ceturnon}$) based on the turn-off current ($i_{ceturnoff}$) by cross-correlation (between respective mirror currents and corresponding determined turn-on and turn-off currents, such as from step S111 or the combination of S108 and S110, or by the degree of deviation (e.g., average, mean, mode or median deviation) of any proportionality constant (between respective mirror currents and corresponding determined turn-on and turn-off currents).

FIG. 8 discloses a chart of a number of power cycles 801 for an inverter (complete on and off cycles for the switching transistors (61, 62, 63, 64, 65)) on the vertical axis versus the cumulative change in temperature ($\Delta T_j$) 802 of its transistors. The number of power cycles 801 can be proportional to the duration of operation of the inverter 50. The power cycle data associated with the power cycling curve 803 of FIG. 8 may be calculated as a data file, a look-up table, a quadratic equation, or as a chart. The power cycle data includes the cumulative number of power cycles versus the cumulative change in temperature ($\Delta T_j$) as input to a transistor longevity estimator stored in the data storage device 16 and executed by the data processor 12. The power cycles 801 can be counted by a counter 77, timer, or data processor 12 associated with the gate driver 18 or the controller 10; the cumulative change in temperature ($\Delta T_j$) is determined in accordance with any method, step or process disclosed in this document.

Once the transistor die temperature or junction temperature is determined, the data processor 12 can use the die temperature for real-time estimation of damage within each transistor for each increase in cumulative Delta Temp ($\Delta T_j$). The power cycle data of FIG. 8 can be estimated by or provided to data processor to predict the remaining life or longevity of a transistor or inverter. The predicted remaining life or longevity of the inverter can be used for scheduling maintenance of the inverter or electric drive-train on a vehicle, for instance.

In one embodiment, an optional counter 77 counts a number of power cycles of the transistor (61, 62, 63, 64, 65, 66) or a group of transistors in an inverter 50. The data processor 12 determines a cumulative change in temperature for the transistor for the power cycles or for a group of transistors in the inverter 50. The data processor 12 predicts a remaining life or longevity of the transistor or an associated inverter based on the counted number of power cycles and the determined cumulative change in the temperature by reference to a look-up table, a database, a file or other records stored in the data storage device 16.

The method and system of this disclosure is well suited for rapid, accurate estimates of transistor temperature during steady-state and transient operating conditions of inverter fed electric motor/generator. Because the method and system of the disclosure does not require a conventional current sensor for current measurements, any error caused by the current sensor is eliminated. Typical errors from current sensors, such as Hall effect sensors, can include any temperature-related drift in measurement of current.

The method and system of this disclosure can operate over an extensive operating temperature range (e.g., −40° C. to 175° C.) of transistor junction; which may be a greater operating range than available from a thermally sensitive resistor or thermistor. For example, because of the limitations of a thermally sensitive resistor sensed temperature below 0° C. might be declared as cold and sensed temperature above 95° C. might be declared as hot due to lack of any resolution in readings below 0° C. and above 95° C. Accordingly, the method and system are well suited for operation with silicon carbide (SiC) power semiconductor devices or other wide band gap semiconductor material that are expected to operate up to 200° C. junction temperature. In certain applications, a conventional temperature sensor (e.g., thermistor) would not be able to maintain accuracy and linearity over the range of −40° C. to 200° C. In such cases the method and system of this disclosure might facilitate obtaining linear range with an acceptable level of accuracy in temperature sensing wide band gap semiconductor junction.

The method and system has low or minimal switching losses because the only a first current flowing through $R_{CLAMP}$ in FIG. 1 is required to implement the temperature sensing scheme, where the first current is much lower than the current at the output of the transistor. The detection circuitry 60 facilitates snubbing or dissipation of the transistor over-voltage during turn-off events. For example, in accordance with the detection circuitry, the over-voltage across transistor is typically less than 200 nano-seconds, however, dv/dt across transistor lasting about 200 nano-seconds is enough to determine junction temperature during turn-off event ($T_{joff}$). The temperature estimation system and method does not require placement of the temperature sensor (thermistor or negative temperature coefficient device) spaced closer to the junction or channel of the transistor that might otherwise reduce required electrical insulation/isolation; hence, reliability of the semiconductor device or the inverter. Accordingly, the temperature estimation system and the method is well-suited for promoting managed thermal performance, densely-packaged power output, and safety of the semiconductor device and the inverter.

Example embodiments being thus described, it will be obvious that the same may be varied in many ways. Such variations are not to be regarded as a departure from the spirit and scope of example embodiments, and all such modifications as would be obvious to one skilled in the art are intended to be included within the scope of the claims.

The following is claimed:

1. A method for estimating junction temperature or die temperature of a transistor of an inverter system, the method comprising:

measuring, by a detector, turn-off change in voltage with respect to change in time between a collector and emitter of a transistor in a phase of an inverter;

measuring, by the detector, peak voltage of the transistor between the collector and the emitter, where the measuring of peak voltage of the transistor between the collector and the emitter is triggered by a drop in a voltage applied to a base or a gate of the transistor in an active state; and where upon the triggering the peak voltage of a transient spike in a collector voltage of the transistor is measured via a series of cascaded multimode diodes and a resistive voltage divider;

determining, by an electronic data processor, intermediate parameters of turn-off current, the turn-on current and on-state voltage drop based on the turn-off voltage change and the peak voltage;

determining, by the data processor, the power loss or energy loss for one switching cycle of the transistor based on the turn-off current, the turn-on current and on-state voltage drop between the collector and emitter of the transistor; and estimating, by the data processor, an associated average junction or die temperature for the transistor over the switching cycle based on the determined energy loss, observed inverter system temperature and thermal characteristic of the inverter system, where an inverter system temperature sensor measures a coolant temperature in a coolant system for cooling the inverter or a housing temperature of an inverter housing.

2. The method for estimating junction temperature according to claim 1 wherein the determining intermediate parameters further comprises:

estimating the junction or die temperature during turn-off of the transistor based on the measured turn-off change in voltage;

determining turn-off time based on the turn-off change in voltage with respect to change in time and based on the estimated junction temperature during turn-off;

determining turn-off current based on the turn-off time and the peak voltage; and determining turn-on current based on the turn-off current, inverter parameters, motor parameters, and motor voltage.

3. The method according to claim 1 wherein the measuring of the turn-off change in voltage or voltage rise with respect to change in time is triggered by a drop in a voltage applied to a base or a gate of the transistor in an active state; and upon the triggering a transient spike of voltage rise with respect to time in a collector voltage of the transistor is measured via a series of cascaded multimode diodes and a resistive voltage divider.

4. The method according to claim 1 wherein the inverter system temperature comprises the coolant temperature and wherein the thermal characteristic comprises a thermal resistance associated with the inverter system.

5. The method according to claim 1 wherein the inverter system temperature comprises the housing temperature of an inverter housing and wherein the thermal characteristic comprises a thermal resistance associated with the inverter system.

6. The method according to claim 1 wherein the determining of the intermediate parameters further comprises:

sampling or measuring voltage between a collector and emitter of the transistor at a capacitor coupled to the collector via a resistor and a diode; and providing the sampled or measured voltages to the data processor via one or more data ports to facilitate estimation of an on-state power loss of the transistor.

7. The method according to claim 6 further comprising: sampling or measuring a voltage at a base or gate of the transistor to facilitate estimation of an on-state power loss of the transistor.

8. The method according to claim 1 further comprising: measuring an observed mirror current of a transistor to cross check or verify a correctness and accuracy of the determined transistor turn-off current and the determined transistor turn-on current by cross-correlation between respective mirror currents and corresponding determined turn-on and turn-off currents or by a degree of deviation from an proportionality constant.

9. The method according to claim 1 further comprising: counting a number of power cycles of the transistor;

determining a cumulative change in temperature for the transistor for the power cycles;

predicting a remaining life or longevity of the transistor or an associated inverter based on the counted number of power cycles and the determined cumulative change in the temperature.

10. A method for estimating junction temperature or die temperature of a transistor of an inverter system, the method comprising:

measuring, by a detector, a turn-off change in voltage ($dv_{ce}/dt$) with respect to change in time between a collector and emitter of a transistor in a phase of an inverter;

measuring, by the detector, a peak voltage ($v_{cepeak}$) of the transistor between the collector and the emitter, where the measuring of the peak voltage ($v_{cepeak}$) of the transistor is triggered by a drop in $v_{ge}$, or a voltage applied to a base or a gate of the transistor in an active state; and upon the triggering the peak voltage of a transient spike in a collector voltage of the transistor is measured via a series of cascaded multimode diodes and a resistive voltage divider;

determining, by an electronic data processor, intermediate parameters of turn-off current ($i_{ceturnoff}$), the turn-on current ($i_{ceturnon}$) and on-state voltage drop ($v_{ceon}$) based on the turn-off voltage change ($dv_{ce}/dt$) and the peak voltage ($v_{cepeak}$);

determining, by the data processor, the power or energy loss for one switching cycle of the transistor based on the turn-off current ($i_{ceturnoff}$), the turn on current ($i_{ceturnon}$) and on-state voltage drop ($v_{ceon}$) between the collector and emitter of the transistor; and estimating, by the data processor, an associated average junction or die temperature for the transistor over the switching cycle based on the determined energy loss, observed inverter system temperature and thermal characteristic of the inverter system, where an inverter system temperature sensor measures a coolant temperature in a coolant system for cooling the inverter or a housing temperature of an inverter housing.

11. The method for estimating junction temperature according to claim 10 wherein the determining intermediate parameters further comprises:

estimating the junction or die temperature during turn-off ($T_{joff}$) of the transistor based on the measured turn-off change in voltage ($dv_{ce}/dt$);

determining turn-off time ($t_{off}$) based on the turn-off change in voltage with respect to change in time ($dv_{ce}/dt$) and based on the estimated junction temperature during turn-off ($t_{joff}$);

determining turn-off current ($i_{ceturnoff}$) based on the turn-off time ($t_{off}$) and the peak voltage ($v_{cepeak}$); and determining turn-on current ($i_{ceturnon}$) based on the turn-off current ($i_{centurnoff}$), inverter parameters, motor parameters, and motor voltage.

12. The method according to claim 10 wherein the measuring of the turn-off change in voltage or voltage rise with respect to change in time ($dv_{ce}/dt$) is triggered by a drop in $v_{ge}$ or a voltage applied to a base or a gate of the transistor in an active state; and upon the triggering a transient spike of voltage rise with respect to time in a collector voltage of the transistor is measured via a series of cascaded multimode diodes and a resistive voltage divider.

13. A method for estimating junction temperature or die temperature of a field effect transistor of an inverter system, the method comprising:

measuring, by a detector, turn-off change in voltage with respect to change in time between a drain and source of a field effect transistor in a phase of an inverter;

measuring, by the detector, peak voltage of the field effect transistor between the drain and the source, where the measuring of the peak voltage of the field effect transistor between the drain and source is triggered a drop in a voltage applied to gate of the field effect transistor in an active state; and where upon the triggering the peak voltage of a transient spike in a drain voltage of the field effect transistor is measured via a series of cascaded multimode diodes and a resistive voltage divider;

determining, by an electronic data processor, intermediate parameters of turn-off current, the turn-on current and on-state voltage drop based on the turn-off voltage change and the peak voltage;

determining, by the data processor, the power or energy loss for one switching cycle of the field effect transistor based on the turn-off current, the turn-on current and on-state voltage drop between the drain and source of the field effect transistor; and estimating, by the data processor, an associated average junction or die temperature for the transistor over the switching cycle based on the determined energy loss, observed inverter system temperature and thermal characteristic of the inverter system with an inverter system temperature sensor that measures a coolant temperature in a coolant system for cooling the inverter or a housing temperature of an inverter housing.

14. The method for estimating junction temperature according to claim 13 wherein the determining intermediate parameters further comprises:

estimating the junction or die temperature during turn-off of the field effect transistor based on the measured turn-off change in voltage;

determining turn-off time based on the turn-off change in voltage with respect to change in time and based on the estimated junction temperature during turn-off;

determining turn-off current based on the turn-off time and the peak voltage; and determining turn-on current based on the turn-off current, inverter parameters, motor parameters, and motor voltage.

15. The method according to claim 13 wherein the measuring of the turn-off change in voltage or voltage rise with respect to change in time is triggered by a drop in a voltage applied to a gate of the field effect transistor in an active state; and upon the triggering a transient spike of voltage rise with respect to time in a drain voltage of the field effect transistor is measured via a series of cascaded multimode diodes and a resistive voltage divider.

16. The method according to claim 13 wherein the inverter system temperature comprises a coolant temperature and wherein the thermal characteristic comprises a thermal resistance associated with the inverter system.

17. The method according to claim 1 wherein the inverter system is without any temperature sensor spaced near the junction of the transistor that might otherwise reduce electrical isolation or lack accuracy over an entire operating range of temperature for the transistor.

* * * * *